United States Patent
Subrahmanian et al.

(10) Patent No.: US 12,268,677 B2
(45) Date of Patent: Apr. 8, 2025

(54) 4-AMINOPYRIDINE (4-AP) AND BONE MORPHOGENETIC PROTEIN 2 (BMP-2)

(71) Applicant: The Penn State Research Foundation, University Park, PA (US)

(72) Inventors: Sandeep Moothedath Subrahmanian, University Park, PA (US); Prem Kumar Govindappa, University Park, PA (US); John Elfar, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 56 days.

(21) Appl. No.: 18/140,258

(22) Filed: Apr. 27, 2023

(65) Prior Publication Data

US 2023/0346758 A1  Nov. 2, 2023

Related U.S. Application Data

(60) Provisional application No. 63/335,349, filed on Apr. 27, 2022.

(51) Int. Cl.
*A61K 31/4409* (2006.01)
*A61P 19/08* (2006.01)

(52) U.S. Cl.
CPC .......... *A61K 31/4409* (2013.01); *A61P 19/08* (2018.01)

(58) Field of Classification Search
CPC ........................... A61K 31/4409; A61P 19/08
See application file for complete search history.

(56) References Cited

U.S. PATENT DOCUMENTS

| | | | |
|---|---|---|---|
| 5,886,005 A | 3/1999 | Aster et al. | |
| 6,004,573 A | 12/1999 | Rathi et al. | |
| 8,460,646 B2 | 6/2013 | Shi et al. | |
| 9,993,429 B2* | 6/2018 | Elfar ................. | A61K 47/34 |
| 11,654,110 B2* | 5/2023 | Elfar ................. | A61K 9/7007 |
| | | | 546/311 |
| 2003/0220345 A1 | 11/2003 | Hamby et al. | |
| 2004/0006082 A1 | 1/2004 | Harada et al. | |
| 2007/0010547 A1 | 1/2007 | Weinstein | |
| 2012/0225875 A1 | 9/2012 | Jonczyk et al. | |
| 2012/0231099 A1 | 9/2012 | Castiel et al. | |
| 2012/0316166 A1 | 12/2012 | Jonczyk et al. | |
| 2015/0032045 A1 | 1/2015 | Yuste et al. | |
| 2015/0352100 A1 | 12/2015 | Bigliardi et al. | |
| 2018/0125781 A1 | 5/2018 | Ye et al. | |
| 2018/0264083 A1 | 9/2018 | Elfar et al. | |
| 2018/0271847 A1* | 9/2018 | Noble ............... | A61K 45/06 |
| 2018/0271934 A1 | 9/2018 | Clark et al. | |
| 2019/0224266 A1* | 7/2019 | Lin-Shiau .......... | A61K 31/5415 |
| 2019/0328824 A1 | 10/2019 | Radisic et al. | |
| 2020/0197488 A1 | 6/2020 | Cotsarelis et al. | |
| 2020/0237709 A1 | 7/2020 | Huber | |
| 2023/0058178 A1* | 2/2023 | Manto ................ | A61K 47/34 |
| 2023/0285299 A1* | 9/2023 | Elfar ................. | A61K 45/06 |
| 2023/0338346 A1* | 10/2023 | Guddadarangaiah ....................... | |
| | | | A61K 31/4409 |
| 2024/0024216 A1* | 1/2024 | Elfar ................. | A61K 8/4926 |
| 2024/0058312 A1* | 2/2024 | Guddadarangaiah ... | A61P 19/08 |

FOREIGN PATENT DOCUMENTS

| | | |
|---|---|---|
| CN | 109876146 | 6/2019 |
| KR | 10-0789560 | 12/2007 |
| WO | WO 1992/009259 | 6/1992 |
| WO | WO 2008/110872 | 9/2008 |
| WO | WO 2013/148740 | 10/2013 |
| WO | WO 2014/151752 | 9/2014 |
| WO | WO 2017/059309 | 4/2017 |
| WO | WO 2018/005257 | 1/2018 |
| WO | WO 2020/058217 | 3/2020 |
| WO | WO 2021/150773 | 7/2021 |
| WO | WO 2022/150349 | 7/2022 |
| WO | WO 2022/150415 | 7/2022 |

OTHER PUBLICATIONS

Expert Opinion on Investigational Drugs, 2009, 18:7, 1013-1024 (Year: 2009).*
J Nippon Med Sch 2017; 84 (1), 12-18 (Year: 2017).*
Biochem Biophys Res Commun, 2010, 394, 1093-1097 (Year: 2010).*
Am J Physiol Lung Cell Mol Physiol, 2006, 291, L993-L1004 (Year: 2006).*
Eur J Physiol (2015) 467: 1663-1676 (Year: 2015).*
Agoston et al., "Effects of 4-aminopyridine in Eaton Lambert Syndrome," Br. J. Anaesth., Apr. 1978, 50(4):383-385.
Agrawal et al., "A review on carrier systems for bone morphogenetic protein-2," J. Biomed. Mat. Res. Part B: Appl. Biomater., May 2017, 105(4):904-925.
Alvites et al., "Peripheral nerve injury and axonotmesis: State of the art and recent advances," Cogent Medicine, Apr. 2018, 5(1):1466404, 45 pages.
Aminoff, "Electrophysiologic Testing for the Diagnosis of Peripheral Nerve Injuries," Anesthesiology: The Journal of the American Society of Anesthesiologists, May 2004, 100(5):1298-1303.
Ashkani-Esfahani et al., "Verapamil, a Calcium-Channel Blocker, Improves the Wound Healing Process in Rats with Excisional Full-Thickness Skin Wounds Based on Stereological Parameters," Adv. Ski. Wound Care, Aug. 2016, 29(8):271-274.

(Continued)

*Primary Examiner* — Jeffrey H Murray
*Assistant Examiner* — Daniel John Burkett
(74) *Attorney, Agent, or Firm* — Fish & Richardson P.C.

(57) ABSTRACT

This document relates to methods and materials for using 4-aminopyridine (4-AP) and/or one or more derivatives of 4-AP. For example, a composition containing 4-AP and/or one or more derivatives of 4-AP can be administered (e.g., orally administered) to a mammal to increase a level of bone morphogenetic protein 2 (BMP-2) polypeptides within the mammal. For example, a composition containing 4-AP and/or one or more derivatives of 4-AP can be administered (e.g., orally administered) to a mammal having bone loss to increase the level of BMP-2 within the mammal, thereby treating the mammal's bone loss.

9 Claims, 8 Drawing Sheets

(56) References Cited

OTHER PUBLICATIONS

Ashrafi et al., "The Role of Neuromediators and Innervation in Cutaneous Wound Healing," Acta Derm. Venereol., Jun. 2016, 96(5):587-594.
Asplund et al., "Incidence of traumatic peripheral nerve injuries and amputations in Sweden between 1998 and 2006," Neuroepidemiology, Jan. 2009, 32(3):217-228.
Ayekoloye et al., "Ultrasound-Guided Versus Anatomic Landmark-Guided Steroid Injection of the Subacromial Bursa in the Management of Subacromial Impingement: A Systematic Review of Randomised Control Studies," Indian J. Orthop., Sep. 2020, 54(Suppl 1):10-19.
Bader et al., "Interactive role of trauma cytokines and erythropoietin and their therapeutic potential for acute and chronic wounds," Rejuvenation Res., Feb. 2011, 14(1):57-66.
Bagheri et al., "Azelnidipine, a new calcium channel blocker, promotes skin wound healing in diabetic rats," J. Surg. Res., Jul. 2011, 169(1):e101-e107.
Barile et al., "Anaesthetics, steroids and platelet-rich plasma (PRP) in ultrasound-guided musculoskeletal procedures," Br. J. Radiol., Sep. 2016, 89(1065):20150355.
Becker et al., "p75 Neurotrophin Receptor: A Double-Edged Sword in Pathology and Regeneration of the Central Nervous System," Vet. Pathol., Jun. 2018, 55(6):786-801.
Bei et al., "Restoration of Visual Function by Enhancing Conduction in Regenerated Axons," Cell, Jan. 2016, 164(1-2):219-232.
Beltran et al., "Fate of combat nerve injury," J Orthop Trauma, Nov. 2012, 26(11):e198-203.
Bentley et al., "p75 Is Important for Axon Growth and Schwann Cell Migration during Development," J. Neurosci., Oct. 2000, 20(20):7706-7715.
Bhaskar et al., "Effect of nifedipine and amlodipine on dead space wound healing in rats," Indian J. Exp. Biol., Mar. 2005, 43(3):294-296.
Bhaskar et al., "Effect of nifedipine and amlodipine on wound healing in rats," Indian J. Physiol. Pharmacol., Jan. 2004, 48(1):111-114.
Birch et al., "Nerve injuries sustained during warfare: part I—Epidemiology," J. Bone Joint Surg. Br., Apr. 2012, 94(4):523-528.
Bishop et al., "Management of radial nerve palsy associated with humeral shaft fracture: a decision analysis model," J. Hand Surg. Am., Jul.-Aug. 2009, 34(6):991-996.
Bonin et al., "A simplified up-down method (SUDO) for measuring mechanical nociception in rodents using von Frey filaments," Mol. Pain, Apr. 2014, 10:26, 10 pages.
Borah et al., "Risedronate preserves bone architecture in postmenopausal women with osteoporosis as measured by three-dimensional microcomputed tomography," Bone, Apr. 2004, 34(4):736-746.
Bose et al., "Keratin k15 as a biomarker of epidermal stem cells," Int. J. Mol. Sci., Sep. 2013, 14(10):19385-19398.
Bostock et al., "The effects of 4-aminopyridine and tetraethylammonium ions on normal and demyelinated mammalian nerve fibres," J. Physiol., 1981, 313:301-315.
Bremer et al., "Sox10 is required for Schwann-cell homeostasis and myelin maintenance in the adult peripheral nerve," Glia, Jul. 2011, 59(7):1022-1032.
Brose et al., "Ultrasound-Guided Steroid Injection of the Pisotriquetral Joint: A Multidisciplinary Effort," Am. J. Phys. Med. Rehabil., Dec. 2017, 96(12):904-907.
Buhl et al., "Potassium channel conductance: a mechanism affecting hair growth both in vitro and in vivo," J. Invest. Dermatol., Mar. 1992, 98(3):315-319.
Campbell, "Evaluation and management of peripheral nerve injury," Clin. Neurophysiol., Sep. 2008, 119(9):1951-1965.
Chen et al., "Thermosensitive cross-linked polymer vesicles for controlled release system," New Journal of Chemistry, Feb. 2006, 30(4):577-582.
Chen et al., "NGF accelerates cutaneous wound healing by promoting the migration of dermal fibroblasts via the PI3K/Akt-Rac1-JNK and ERK pathways," Biomed. Res. Int., May 2014, 2014:547187, 13 pages.
Chen et al., "On the mechanism by which 4-Aminopyridine occludes quinidine block of the cardiac K+ channel, hKv1.5," J. Gen. Physiol., Apr. 1998, 111(4):539-554.
Chen et al., "The murine excisional wound model: Contraction revisited," Wound Repair Regen., Nov.-Dec. 2015, 23(6):874-877.
Chen et al., "Thermoviscosifying polymer used for enhanced oil recovery: Rheological behaviors and core flooding test," Polymer Bulletin, Feb. 2012, 70(2):391-401.
Chenu, "Role of innervation in the control of bone remodeling," J Musculoskelet Neuronal Interact., Jun. 2004, 4(2):132-134.
Cheret et al., "Role of neuropeptides, neurotrophins, and neurohormones in skin wound healing," Wound Repair Regen., Nov.-Dec. 2013, 21(6):772-788.
Chung et al., "Peripheral neuropathy: clinical and electrophysiological considerations," Neuroimaging Clin N Am., Feb. 2014, 24(1):49-65.
Clark et al., "Transdermal delivery of 4-aminopyridine accelerates motor functional recovery and improves nerve morphology following sciatic nerve crush injury in mice," Neural Regen. Res., Jan. 2020, 15(1):136-144.
Davis et al., "Mechanism of action of 4-aminopyridine in the symptomatic treatment of multiple sclerosis," Ann. Neurol., May 1995, 37(5):684.
Davis et al., "Orally administered 4-aminopyridine improves clinical signs in multiple sclerosis," Ann Neurol., Feb. 1990, 27(2):186-192.
De Giglio et al., "Aminopiridines in the treatment of multiple sclerosis and other neurological disorders," Neurodegener. Dis. Manag., Oct. 2020, 10(6):409-23.
DeForge et al., "Effect of 4-aminopyridine on gait in ambulatory spinal cord injuries: a double-blind, placebo-controlled, crossover trial, " Spinal Cord, Dec. 2004, 42(12):674-685.
Demidova-Rice et al., "Wound Healing Angiogenesis: Innovations and Challenges in Acute and Chronic Wound Healing," Adv. Wound Care (New Rochelle), Feb. 2012, 1(1):17-22.
Dietrich et al., "Neuroprotective Properties of 4-Aminopyridine," Neurol Neuroimmunol Neuroinflamm, Mar. 2021, 8(3):e976, 7 pages.
Dietrich et al., "Protective effects of 4-aminopyridine in experimental optic neuritis and multiple sclerosis," Brain, Apr. 2020, 143(4):1127-1142.
Ding et al., "Electrospun polymer biomaterials," Progress in Polymer Science, 90:1-34.
Doshi et al., "Wound healing from a cellular stress response perspective," Cell Stress Chaperones, Dec. 2008, 13(4):393-399.
Douglas, "TGF-β in wound healing: A review," J. Wound Care, Sep. 2010, 19(9):403-406.
Dunn et al., "Dalfampridine: a brief review of its mechanism of action and efficacy as a treatment to improve walking in patients with multiple sclerosis," Curr. Med. Res. Opin., Jul. 2011, 27(7):1415-1423.
Ehsanian et al., "Ultrasound-guided cervical selective nerve root injections: a narrative review of literature," Reg. Anesth. Pain Med., May 2021, 46(5):416-421.
Eisenberg et al., "Calcium channel blockers: an update," Am. J. Med., Jan. 2004, 116(1):35-43.
Elfar et al., "4-Aminopyridine Induces Nerve Growth Factor to Improve Skin Wound Healing and Tissue Regeneration," Biomedicines, Jul. 2022, 10(7):1649, 19 pages.
Elfar et al., "Erythropoietin accelerates functional recovery after peripheral nerve injury," J. Bone Joint Surg. Am., Aug. 2008, 90(8):1644-1653.
Eming et al., "Wound repair and regeneration: Mechanisms, signaling, and translation," Science, Dec. 2014, 6(265):265sr6.
Engel et al., "Trophic functions of the neuron. II. Denervation and regulation of muscle. Morphological effects of denervation of muscle. A quantitative ultrastructural study," Ann. N.Y. Acad. Sci., Mar. 1974, 228(0):68-88.
Espejo et al., "Dalfampridine in multiple sclerosis: From symptomatic treatment to immunomodulation," Clin. Immunol., Jan. 2012, 142(1):84-92.

(56) References Cited

OTHER PUBLICATIONS

Evans et al., "Epithelial mechanobiology, skin wound healing, and the stem cell niche," J. Mech. Behav. Biomed. Mater., Dec. 2013, 28:397-409.
Extended European Search Report in European Appln. No. 21744391.0, dated Sep. 28, 2023, 11 pages.
Extended European Search Report in European Appln. No. 22737021.0, dated Jun. 5, 2024, 10 pages.
Extended European Search Report in European Appln. No. 24172862.5, dated Sep. 27, 2024, 8 pages.
Franciosi et al., "Broad-Spectrum Effects of 4-Aminopyridine to Modulate Amyloid β1-42-Induced Cell Signaling and Functional Responses in Human Microglia," J. Neurosci., Nov. 2006, 26(45):11652-11664.
Fujiwara et al., "SOX10 transactivates S100B to suppress Schwann cell proliferation and to promote myelination," PLoS ONE, Dec. 2014, 9(12):e115400, 17 pages.
Garcia et al., "NF-M is an essential target for the myelin-directed "outside-in" signaling cascade that mediates radial axonal growth," J. Cell. Biol., Dec. 2003, 163(5):1011-1020.
García-Castellano et al., "Is Bone a Target-Tissue For the Nervous System? New Advances on the Understanding of Their Interactions," Iowa Orthopaed. J, Feb. 2000, 20:49-58.
GenBank Accession No. P12643, "Bone morphogenetic protein 2," Dec. 5, 2018, 7 pages.
Goodman et al., "A phase 3 trial of extended release oral dalfampridine in multiple sclerosis," Ann. Neurol., Oct. 2010, 68(4):494-502.
Goodman et al., "Dose comparison trial of sustained-release fampridine in multiple sclerosis," Neurology, Oct. 2008, 71(15):1134-1141.
Goodman et al., "Enhancing Neural Transmission in Multiple Sclerosis (4-Aminopyridine Therapy)," Neurotherapeutics, Jan. 2013, 10(1):106-110.
Goodman et al., "Sustained-release oral fampridine in multiple sclerosis: a randomised, double-blind, controlled trial," Lancet, Feb. 2009, 373(9665):732-738.
Gordon et al., "The basis for diminished functional recovery after delayed peripheral nerve repair," J. Neurosci., Apr. 2011, 31(14):5325-5234.
Gordon et al., "The potential of electrical stimulation to promote functional recovery after peripheral nerve injury—comparisons between rats and humans," Acta Neurochir. Suppl., 2007, 100:3-11.
Gostynska et al., "The pleiotropic molecule NGF regulates the in vitro properties of fibroblasts, keratinocytes, and endothelial cells: Implications for wound healing," Am. J. Physiol.-Cell Physiol., Feb. 2020, 318(2):C360-C371.
Govindappa et al., "An effective erythropoietin dose regimen protects against severe nerve injury-induced pathophysiological changes with improved neural gene expression and enhances functional recovery," Int Immunopharmacol., Mar. 2020, 82:106330.
Govindappa et al., "Effects of 4-Aminopyridine on Combined Nerve and Muscle Injury and Bone Loss," J. Hand Surg. Am., Aug. 2023, 48(8):831.e1-831.e9.
Govindappa et al., "The Potential Repurposing Effect 4-Aminopyridine in Nerve and Muscle Injury-induced Bone Loss," Special Issue: Experimental Biology 2021 Meeting Abstracts, May 2021, 35(1), 3 pages (Abstract Only).
Grässel, "The role of peripheral nerve fibers and their neurotransmitters in cartilage and bone physiology and pathophysiology," Arthritis Res Ther., Nov. 2014, 16(6):485, 13 pages.
Gresset et al., "Boundary Caps Give Rise to Neurogenic Stem Cells and Terminal Glia in the Skin," Stem Cell Reports, Aug. 2015, 5(2):278-90.
Grijalva et al., "Efficacy and Safety of 4-Aminopyridine in Patients with Long-Term Spinal Cord Injury: A Randomized, Double-Blind, Placebo-Controlled Trial," Pharmacotherapy, Jul. 2003, 23(7):823-834.
Grijalva et al., "High Doses of 4-Aminopyridine Improve Functionality in Chronic Complete Spinal Cord Injury Patients with MRI Evidence of Cord Continuity," Arch. Med. Res., Oct. 2010, 41(7):567-575.
Grimaldi et al., "Mobilization of calcium from intracellular stores, potentiation of neurotransmitter-induced calcium transients, and capacitative calcium entry by 4-aminopyridine," J. Neurosci., May 2001, 21(9):3135-3143.
Grose et al., "A crucial role of B1 integrins for keratinocyte migration in vitro and during cutaneous wound repair," Development, May 2002, 129(9):2303-2315.
Gruner et al., "4-Aminopyridine enhances motor evoked potentials following graded spinal cord compression injury in rats," Brain Res, Jan. 1999, 816(2):446-456.
Gurjar et al., "4-Aminopyridine: A Single-Dose Diagnostic Agent to Differentiate Axonal Continuity in Nerve Injuries," Mil. Med., Jan.-Feb. 2021, 186(Suppl 1):479-485.
Gurtner et al., "Wound repair and regeneration," Nature, May 2008, 453(7193):314-321.
Hadjichristidis et al., "Macromolecular architectures by living and controlled/living polymerizations," Progress in Polymer Science, Dec. 2006, 31(12):1068-1132.
Hamed et al., "Erythropoietin, a novel repurposed drug: an innovative treatment for wound healing in patients with diabetes mellitus," Wound Repair Regen., Dec. 2013, 22(1):23-33.
Hamed et al., "Topical erythropoietin promotes wound repair in diabetic rats," J. Invest. Dermatol., Jan. 2010, 130(1):287-294.
Hansebout et al., "4-Aminopyridine in chronic spinal cord injury: A controlled, double-blind, crossover study in eight patients," J. Neurotrauma, Feb. 1993, 10(1):1-18.
Hartung et al., "4-Aminopyridine is not just a symptomatic therapy, it has a neuroprotective effect—Commentary," Mult. Scler., Jul. 2020, 26(11):1312-1314.
Hauser et al., "4-aminopyridine: new life for an old drug," Ann. Neurol., Jul. 2010, 68(1):A8-A9.
Hayes, "Fampridine-SR for multiple sclerosis and spinal cord injury," Expert Rev. Neurother., May 2007, 7(5):453-461.
Hayes, "The use of 4-aminopyridine (fampridine) in demyelinating disorders," CNS Drug. Rev., Dec. 2004, 10(4):295-316.
Hemmati et al., "Wound healing potential of topical amlodipine in full thickness wound of rabbit," Jundishapur J. Nat. Pharm. Prod., Aug. 2014, 9(3):e15638, 4 pages.
Henrot et al., "A Method for Isolating and Culturing Skin Cells: Application to Endothelial Cells, Fibroblasts, Keratinocytes, and Melanocytes From Punch Biopsies in Systemic Sclerosis Skin," Front. Immunol., Oct. 2020, 11:566607, 12 pages.
Heywood et al., "In ovo neuromuscular stimulation alters the skeletal muscle phenotype of the chick," J. Muscle Res. Cell. Motil., 2005, 26(1):49-56.
Hong et al., "The Role of Hypoxia-Inducible Factor in Wound Healing," Adv. Wound Care (New Rochelle), May 2014, 3(5):390-399.
Houshyar et al., "Peripheral Nerve Conduit: Materials and Structures," ACS Chem. Neurosci., Aug. 2019, 10(8):3349-3365.
Hsu et al., "Human equivalent dose of oral 4-aminopyridine differentiates nerve crush injury from transection injury and improves post-injury function in mice," Neural. Regen. Res., Nov. 2020, 15(11):2098-2107, 13 pages.
Hu et al., "Involvement of the 4-aminopyridine-sensitive transient A-type K+ current in macrophage-induced neuronal injury," Eur. J. Neurosci., Jan. 2010, 31(2):214-222.
Hwee et al., "Fast skeletal muscle troponin activator tirasemtiv increases muscle function and performance in the B6SJL-SOD1G93A ALS mouse model," PLoS One, May 2014, 9(5):e96921, 9 pages.
Ikeda et al., "The relationship between nerve conduction velocity and fiber morphology during peripheral nerve regeneration," Brain Behav., Jul. 2012, 2(4):382-390.
International Preliminary Report on Patentability in International Appln. No. PCT/US2021/014442, mailed on Aug. 4, 2022, 9 pages.
International Preliminary Report on Patentability in International Appln. No. PCT/US2022/011262, mailed on Jul. 20, 2023, 6 pages.
International Preliminary Report on Patentability in International Appln. No. PCT/US2022/011351, mailed on Jul. 20, 2023, 12 pages.

(56) References Cited

OTHER PUBLICATIONS

International Search Report and Written Opinion in International Appln. No. PCT/US2021/014442, mailed on Apr. 20, 2021, 12 pages.
International Search Report and Written Opinion in International Appln. No. PCT/US2022/011262, mailed on Mar. 22, 2022, 16 pages.
International Search Report and Written Opinion in International Appln. No. PCT/US2022/11351, mailed on Mar. 29, 2022, 16 pages.
Ito et al., "Wnt-dependent de novo hair follicle regeneration in adult mouse skin after wounding," Nature, May 2007, 447(7142):316-320, 6 pages.
Jagadeeshaprasad et al., "4-Aminopyridine Induces Nerve Growth Factor to Improve Skin Wound Healing and Tissue Regeneration," Biomedicines, Jul. 2022, 10(7):1649.
Jagadeeshaprasad et al., "Isolation, Culture, and Characterization of Primary Schwann Cells, Keratinocytes, and Fibroblasts from Human Foreskin," J. Vis. Exp., Mar. 2022, 181:e63776.
Jensen et al., "4-Aminopyridine for symptomatic treatment of multiple sclerosis: a systematic review," Ther Adv Neurol Disord, Mar. 2014, 7(2):97-113.
Johnston et al., "Dedifferentiated Schwann Cell Precursors Secreting Paracrine Factors Are Required for Regeneration of the Mammalian Digit Tip," Cell Stem Cell, Oct. 2016, 19(4):433-448.
Kasatkina, "4-aminopyridine sequesters intracellular Ca2+ which triggers exocytosis in excitable and non-excitable cells," Sci. Rep., Oct. 2016, 6:34749, 13 pages.
Kemp et al., "Comparative outcome measures in peripheral regeneration studies," Exp. Neurol., Jan. 2017, 287(Pt 3):348-357.
Khan et al., "The use of recombinant human bone morphogenetic protein-2 (rhBMP-2) in orthopaedic applications," Expert Opin. Biol. Ther., May 2004, 4(5):741-748.
King et al., "4-Aminopyridine Toxicity: a Case Report and Review of the Literature," J Med Toxicol, Sep. 2012, 8(3):314-321.
Kirchhoff et al., "Excitation of cutaneous sensory nerve endings in the rat by 4-aminopyridine and tetraethylammonium," J. Neurophysiol., 1992, 67(1):125-31.
Krishnan et al., "Sustained-release fampridine and the role of ion channel dysfunction in multiple sclerosis," Mult. Scler., Oct. 2012, 19(4):385-91.
Kumar et al., "Neuropeptide Substance P Enhances Skin Wound Healing In Vitro and In Vivo under Hypoxia," Biomedicines, Feb. 2021, 9:222, 12 pages.
Lammertse et al., "Safety and efficacy of oral fampridine-SR (sustained-release 4-aminopyridine) in patients with chronic motor-incomplete spinal cord injury," J. Spinal Cord Med., 2002, 25(Supplement 1):S5.
Landen et al., "Transition from inflammation to proliferation: a critical step during wound healing," Cell. Mol. Life Sci., May 2016, 73(20):3861-3885.
Laverdet et al., "Skin innervation: important roles during normal and pathological cutaneous repair," Histol. Histopathol., Aug. 2015, 30(8):875-892.
Lawman et al., "Nerve growth factor accelerates the early cellular events associated with wound healing," Exp. Mol. Pathol., Oct. 1985, 43(2):274-281.
Leal et al., "Substance P Promotes Wound Healing in Diabetes by Modulating Inflammation and Macrophage Phenotype," Am. J. Pathol., Jun. 2015, 185(6):1638-1648.
Lebonvallet et al., "New insights into the roles of myofibroblasts and innervation during skin healing and innovative therapies to improve scar innervation," Exp. Dermatol, Sep. 2018, 27(9):950-958.
Leung et al., "Potassium channel blocker, 4-aminopyridine-3-methanol, restores axonal conduction in spinal cord of an animal model of multiple sclerosis," Exp Neurol, Jan. 2011, 227(1):232-235.
Leussink et al., "Restoring Axonal Function with 4-Aminopyridine: Clinical Efficacy in Multiple Sclerosis and Beyond," CNS Drugs, Jul. 2018, 32(7):637-651.
Li et al., "Nerve growth factor: acceleration of the rate of wound healing in mice," Proc. Natl. Acad. Sci. USA, Jul. 1980, 77(7):4379-4381.
Li et al., "Potentiation of high voltage-activated calcium channels by 4-aminopyridine depends on subunit composition," Mol. Pharmacol., Dec. 2014, 86(6):760-772.
Lichtman et al., "Transforming growth factor beta (TGF-β) isoforms in wound healing and fibrosis," Wound Repair Regen., Mar. 2016, 24(2):215-222.
Lien et al., "Optimizing skeletal muscle reinnervation with nerve transfer," Hand Clin., Nov. 2008, 24(4):445-454.
Liu et al., "Role of NGF and its receptors in wound healing (Review)," Exp. Ther. Med., Apr. 2021, 21(6):599, 9 pages.
Ljungquist et al., "Radial nerve injuries," J. Hand Surg. Am., Jan. 2015, 40(1):166-172.
Lucas et al., "Differential Roles of Macrophages in Diverse Phases of Skin Repair," J. Immunol., Apr. 2010, 184(7):3964-3977.
Lundh et al., "4-Aminopyridine—a new drug tested in the treatment of Eaton-Lambert syndrome," J. Neurol. Neurosurg. Psychiatry, Nov. 1977, 40(11):1109-1112.
Lundh et al., "Effects of 4-aminopyridine in myasthenia gravis," J. Neurol. Neurosurg. Psychiatry, Feb. 1979, 42(2):171-175.
Manoukian et al., "Aligned microchannel polymer-nanotube composites for peripheral nerve regeneration: Small molecule drug delivery," J. Control Release, Feb. 2019, 296:54-67.
Manoukian et al., "Biopolymer-nanotube nerve guidance conduit drug delivery for peripheral nerve regeneration: In vivo structural and functional assessment," Bioactive Mater., Sep. 2021, 6(9):2881-2893.
Manto et al., "(4-Aminopyridine)-PLGA-PEG as a Novel Thermosensitive and Locally Injectable Treatment for Acute Peripheral Nerve Injury," ACS Appl. Bio Mater., Apr. 2021, 4(5):4140-4151.
Martinov et al., "Measuring changes in tactile sensitivity in the hind paw of mice using an electronic von Frey apparatus," J. Vis. Exp., Dec. 2013, (82):e51212, 6 pages.
Matsuda et al., "Role of nerve growth factor in cutaneous wound healing: Accelerating effects in normal and healing-impaired diabetic mice," J. Exp. Med., Feb. 1998, 187(3):297-306.
Mcheik et al., "Foreskin-isolated keratinocytes provide successful extemporaneous autologous paediatric skin grafts," J. Tissue Eng. Regen. Med., Mar. 2016, 10(3):252-260.
Mikesh et al., "Polyethylene glycol solutions rapidly restore and maintain axonal continuity, neuromuscular structures, and behaviors lost after sciatic nerve transections in female rats," J Neurosci Res, Nov. 2017, 96(7):1-20.
Mirshafiey et al., "Anti-inflammatory property and inhibitory effect of 4-aminopyridine in antibody production in the experimental modal of immune complex-in-duced inflammation," Journal of Chinese Clinical Medicine, 2010, 5(7):450-456.
Motohashi et al., "Sox10 Functions as an Inducer of the Direct Conversion of Keratinocytes Into Neural Crest Cells," Stem Cells Dev, Dec. 2020, 29(23):1510-1519.
Muangman et al., "Nerve growth factor accelerates wound healing in diabetic mice," Wound Repair Regen., Jan.-Feb. 2004, 12(1):44-52.
Murray et al., "Treatment with oral 4-aminopyridine in disorders of neuromuscular transmission," Neurology, Mar. 1981, 31(3):265-271.
Nelson et al., "dsRNA Released by Tissue Damage Activates TLR3 to Drive Skin Regeneration," Cell Stem Cell, Aug. 2015, 17(2):139-151.
Nithya et al., "The effect of nerve growth factor on the early responses during the process of wound healing," Biochimica et Biophysica Acta, Apr. 2003, 1620(1-3):25-31.
Niver et al., "Management of radial nerve palsy following fractures of the humerus," Orthop. Clin. North Am., Jul. 2013, 44(3):419-24.
Noble et al., "4-Aminopyridine as a Single Agent Diagnostic and Treatment for Severe Nerve Crush Injury," Mil Med, Mar. 2019, 184(Suppl 1):379-385.

(56) References Cited

OTHER PUBLICATIONS

Nosbaum et al., "Cutting Edge: Regulatory T Cells Facilitate Cutaneous Wound Healing," J. Immunol., Mar. 2016, 196(5):2010-2014.
Olczyk et al., "The role of the extracellular matrix components in cutaneous wound healing," Biomed. Res. Int., Mar. 2014, 2014:747584, 9 pages.
Page et al., "Potassium channel blockers restore axonal conduction in CNS trauma and diseases," Neural Regen Res, Aug. 2016, 11(8):1226-1227.
Pakyari et al., "Critical Role of Transforming Growth Factor Beta in Different Phases of Wound Healing," Adv. Wound Care, Jun. 2013, 2(5):215-224.
Parameswaran-Thankam et al., "Guar-Based Injectable Thermoresponsive Hydrogel as a Scaffold for Bone Cell Growth and Controlled Drug Delivery," ACS Omega, Nov. 2018, 3(11):15158-15167.
Parfejevs et al., "Injury-activated glial cells promote wound healing of the adult skin in mice," Nat. Commun., Jan. 2018, 9:236, 16 pages.
Partial Supplementary European Search Report in European Appln. No. 22737070.7, dated Jun. 18, 2024, 18 pages.
Pastar et al., "Epithelialization in Wound Healing: A Comprehensive Review," Adv. Wound Care, Jul. 2014, 3(7):445-464.
Paudel et al., "Challenges and opportunities in dermal/transdermal delivery," Ther. Deliv., Jul. 2010, 1(1):109-131.
Paus et al., "Nerve Growth-Factor Modulates Keratinocyte Proliferation in Murine Skin Organ-Culture," Br. J. Dermatol., Feb. 1994, 130(2):174-180.
Peleshok et al., "Neurotrophic factor changes in the rat thick skin following chronic constriction injury of the sciatic nerve," Mol. Pain, Jan. 2012, 8:1, 15 pages.
Penn et al., "The role of the TGF-β family in wound healing, burns and scarring: a review," Int. J. Burns. Trauma, Feb. 2012, 2(1):18-28.
Prausnitz et al., "Transdermal drug delivery," Nat. Biotechnol., Nov. 2008, 26(11):1261-1268.
Raasakka et al., "Molecular structure and function of myelin protein P0 in membrane stacking," Sci. Rep., Jan. 2019, 9(1):642, 15 pages.
Reagan-Shaw et al., "Dose translation from animal to human studies revisited," FASEB J., Mar. 2008, 22(3):659-661.
Rebowe et al., "Nerve Repair with Nerve Conduits: Problems, Solutions, and Future Directions," J. Hand Microsurg., Aug. 2018, 10(2):61-65.
Redkiewicz, "The Regenerative Potential of Substance P," Int. J. Mol. Sci., Jan. 2022, 23(2):750, 14 pages.
Reichner et al., "Determination of the role of hypoxia-inducible factor 1 in wound healing," Methods Enzymol., Feb. 2004, 381:527-538.
Riis et al., "Hypoxia enhances the wound-healing potential of adipose-derived stem cells in a novel human primary keratinocyte-based scratch assay," Int. J. Mol. Med., Mar. 2017, 39(3):587-594.
Rittie, "Cellular mechanisms of skin repair in humans and other mammals," J. Cell Commun. Signal., May 2016, 10(2):103-20.
Rivera et al., "Disability following combat-sustained nerve injury of the upper limb," Bone Joint J., Feb. 2014, 96-B(2):254-258.
Rodrigues et al., "Wound Healing: A Cellular Perspective," Physiol. Rev., Nov. 2018, 99(1):665-706.
Rogawski et al., "Effects of 4-aminopyridine on calcium action potentials and calcium current under voltage clamp in spinal neurons," Brain Res., Nov. 1983, 280(1):180-185.
Rosique et al., "Curbing Inflammation in Skin Wound Healing: A Review," Int. J. Inflamm., Aug. 2015, 2015:316235, 10 pages.
Sakuma et al., "Chronic Electrical Nerve Stimulation as a Therapeutic Intervention for Peripheral Nerve Repair," Bioelectron. Med., Jul. 2015, 2:43-48.
Sanders et al., "Conduction velocity and myelin thickness in regenerating nerve fibres," J. Physiol., Sep. 1946, 105(2):152-174.
Santos et al., "The expression of keratin k10 in the basal layer of the epidermis inhibits cell proliferation and prevents skin tumorigenesis," J. Biol. Chem., May 2002, 277(21):19122-19130.
Schliephake et al., "Effect of immobilized bone morphogenic protein 2 coating of titanium implants on peri-implant bone formation," Clin. Oral Implants Res., Sep. 2005, 16(5):563-569.
Sedehizadeh et al., "The Use of Aminopyridines in Neurological Disorders," Clin. Neuropharmacol., Jul-Aug. 2012, 35(4):191-200.
Shah et al., "Current treatment of radial nerve palsy following fracture of the humeral shaft," J. Hand Surg. Am., Oct. 2008, 33(8):1433-1434.
Sharun et al., "Antibody-based immunotherapeutics and use of convalescent plasma to counter COVID-19: advances and prospects," Expert Opin Biol Ther, Sep. 2020, 20(9):1033-1046.
Shwartz et al., "Cell Types Promoting Goosebumps Form a Niche to Regulate Hair Follicle Stem Cells," Cell, Aug. 2020, 182(3):578-593.
Siebert et al., "Erythropoietin improves skin wound healing and activates the TGF-β signaling pathway," Lab Invest., Dec. 2011, 91(12):1753-1765.
Sindhurakar et al., "Clinically Relevant Levels of 4-Aminopyridine Strengthen Physiological Responses in Intact Motor Circuits in Rats, Especially After Pyramidal Tract Injury," Neurorehabil Neural Repair, Apr. 2017, 31(4):387-396.
Skoff et al., "Nerve growth factor regulates substance P in adult sensory neurons through both TrkA and p75 receptors," Exp. Neurol., Feb. 2006, 197(2):430-436.
Smith et al., "Effects of 4-aminopyridine on demyelinated axons, synapses and muscle tension," Brain, Jan. 2000, 123:171-184.
Sorg et al., "Effects of erythropoietin in skin wound healing are dose related," FASEB J., Sep. 2009, 23(9):3049-3058.
Sorg et al., "Skin Wound Healing: An Update on the Current Knowledge and Concepts," Eur. Surg. Res., Dec. 2016, 58(1-2):81-94.
Spine-Health.com [online], "Sciatic Nerve Anatomy," Dec. 17, 2020, retrieved on Jul. 27, 2023, retrieved from URL<https://www.spine-health.com/conditions/spine-anatomy/sciatic-nerve-anatomy>, 9 pages.
Stratton et al., "Purification and Characterization of Schwann Cells from Adult Human Skin and Nerve," Eneuro, May 2017, 4(3):e307-16, 15 pages.
Strijbis et al., "4-aminopyridine is not just a symptomatic therapy, it has a neuroprotective effect—Yes," Mult. Scler., Jul. 2020, 26(11):1309-1310.
Strupp et al., "Aminopyridines for the treatment of neurologic disorders," Neurol. Clin. Pract., Feb. 2017, 7(1):65-76.
Strupp et al., "Pharmacotherapy of vestibular and cerebellar disorders and downbeat nystagmus: translational and back-translational research," Ann. N.Y. Acad. Sci., Apr. 2015, 1343:27-36.
Supplementary Partial European Search Report in European Appln No. 21744391.0, dated Jun. 27, 2023, 14 pages.
Suvik et al., "The use of modified Masson's trichrome staining in collagen evaluation in wound healing study," Malays. J. Vet. Res., Jan. 2012, 3(1):39-47.
Takeshita et al., "Modified forelimb grip strength test detects aging-associated physiological decline in skeletal muscle function in male mice," Sci. Rep., Feb. 2017, 7:42323, 9 pages.
Taylor et al., "The incidence of peripheral nerve injury in extremity trauma," Am. J. Phys. Med. Rehabil., May 2008, 87(5):381-385.
Togari et al., "The neuro-osteogenic network: The sympathetic regulation of bone resorption," Jap. Dental Sci. Rev, Aug. 2012, 48(2):61-70.
Tong et al., "Keratin 17 modulates hair follicle cycling in a TNFalpha-dependent fashion," Genes Dev, May 2006, 20(10):1353-1364.
Tseng et al., "4-Aminopyridine promotes functional recovery and remyelination in acute peripheral nerve injury," EMBO Mol. Med., Dec. 2016, 8(12):1409-1420.
Uges et al., "4-Aminopyridine kinetics," Clin. Pharmacol. Ther., May 1982, 31(5):587-593.
Van der Bruggen et al., "Randomized trial of 4-aminopyridine in patients with chronic incomplete spinal cord injury," J. Neurol., Aug. 2001, 248:665-671.

(56) References Cited

OTHER PUBLICATIONS

Vivo et al., "Immediate electrical stimulation enhances regeneration and reinnervation and modulates spinal plastic changes after sciatic nerve injury and repair," Exp. Neurol., May 2008, 211(1):180-193.
Vollmer et al., "Steady-state pharmacokinetics and tolerability of orally administered fampridine sustained-release 10-mg tablets in patients with multiple sclerosis: a 2-week, open-label, follow-up study," Clin. Ther., Oct. 2009, 31(10):2215-2223.
Wake et al., "Control of local protein synthesis and initial events in myelination by action potentials," Science, Sep. 2011, 333(6049):1647-1651.
Wallengren et al., "Neuropeptide-containing C-fibres and wound healing in rat skin. Neither capsaicin nor peripheral neurotomy affect the rate of healing, " Br. J. Dermatol., Mar. 1999, 140(3):400-408.
Wan et al., "Short-term low-frequency electrical stimulation enhanced remyelination of injured peripheral nerves by inducing the promyelination effect of brain-derived neurotrophic factor on Schwann cell polarization," J. Neurosci. Res., Sep. 2010, 88(12):2578-2587.
Wang, "Image Guidance Technologies for Interventional Pain Procedures: Ultrasound, Fluoroscopy, and CT," Curr. Pain Headache Rep., Jan. 2018, 22(1):6.
Waxman, "Determinants of conduction velocity in myelinated nerve fibers," Muscle Nerve, Mar.-Apr. 1980, 3(2):141-150.
Werner et al., "Regulation of Wound Healing by Growth Factors and Cytokines," Physiol. Rev., Jul. 2003, 83(3):835-870.
Wikipedia.com [online], "Cutaneous Nerve," Oct. 2018, retrieved on Jul. 27, 2023, retrieved from URL<https://en.wikipedia.org/w/index.php?title=Cutaneous_nerve&oldid=863010836>, 2 pages.
Wikipedia.com [online], "Room Temperature," Mar. 2018, retrieved on Jul. 27, 2023, retrieved from URL<https://en.wikipedia.org/w/index.php?title=Room_temperature&oldid=829684572>, 3 pages.
Wilfong et al., "Nerve growth factor and substance P regulation in nasal sensory neurons after toluene diisocyanate exposure," Am. J. Respir. Cell Mol. Biol., Jul. 2004, 30(6):793-800.
Wu et al., "Aminopyridines Potentiate Synaptic and Neuromuscular Transmission by Targeting the Voltage-activated Calcium Channel beta Subunit," J. Biol. Chem. 2009, 284, 36453-36461.
Wulff, et al., "Voltage-gated potassium channels as therapeutic targets," Nat. Rev. Drug Disc., Dec. 2009, 8(12):982-1001.
Xue et al., "FOXC2 controls Ang-2 expression and modulates angiogenesis, vascular patterning, remodeling, and functions in adipose tissue," Proc. Natl. Acad. Sci. USA, Jul. 2008, 105(29):10167-10172.
Yang et al., "Epidermal Stem Cells in Wound Healing and Regeneration," Stem Cells Int., Jan. 2020, 2020:9148310, 11 pages.
Yeh et al., "The effects of artocarpin on wound healing: In Vitro and in vivo studies, " Sci. Rep., Nov. 2017, 7:15599, 13 pages.
Yoo et al., "Phenomenology of the Initial Burst Release of Drugs from PLGA Microparticles," ACS Biomater. Sci. Eng., Nov. 2020, 6(11):6053-6062.
Youxin et al., "Synthesis and properties of biodegradable ABA triblock copolymers consisting of poly(1-lactic acid) or poly (1-lactic-co-glycolic acid) A-blocks attached to central poly ( oxyethylene ) B-blocks," J. Control. Release, Dec. 1993, 27(3):247-257.
Yuan et al., "Neurofilaments and Neurofilament Proteins in Health and Disease," Cold Spring Harb. Perspect. Biol., Apr. 2017, 9(4):a018309, 26 pages.
Yue et al., "4-Aminopyridine attenuates muscle atrophy after sciatic nerve crush injury in mice," Muscle Nerve, Aug. 2019, 60(2):192-201.
Zhang et al., "Functional Polymer-Based Nerve Guide Conduits to Promote Peripheral Nerve Regeneration," Adv. Mater. Interfaces, May 2020, 7(14):2000225, 21 pages.
Zhang et al., "Potassium channels as potential drug targets for limb wound repair and regeneration," Precis. Clin. Med., Mar. 2020, 3(1):22-33.
Zhao et al., "Spinal D-amino acid oxidase contributes to neuropathic pain in rats," J. Pharmacol. Exp. Ther., Jan. 2010, 332(1):248-254.
Zwierello et al., "Burns: Classification, Pathophysiology, and Treatment: A Review," Int. J. Mol. Sci., Feb. 2023, 24(4):3749.
U.S. Appl. No. 17/759,224, filed Jul. 21, 2022, Kristen Manto, Published as U.S. Publication No. 2023/0058178.
U.S. Appl. No. 18/139,123, filed Apr. 25, 2023, Jagadeeshaprasad Mashanipalya Guddadarangaiah, Published as U.S. Publication No. 2023/0338346.
U.S. Appl. No. 18/270,914, filed Jul. 5, 2023, John Elfar, Published as U.S. Publication No. 2024/0024216.
U.S. Appl. No. 18/270,969, filed Jul. 5, 2023, Jagadeeshaprasad Mashanipalya Guddadarangaiah, Published as U.S. Publication No. 2024/0058312.
Ding et al., "Electrospun polymer biomaterials," Progress in Polymer Science, Mar. 2019, 90:1-34.

\* cited by examiner

4-AMINOPYRIDINE (4-AP) AND BONE MORPHOGENETIC PROTEIN 2 (BMP-2)

CROSS-REFERENCE To RELATED APPLICATIONS

This application claims the benefit of U.S. Patent Application Ser. No. 63/335,349, filed on Apr. 27, 2022. The disclosure of the prior application is considered part of (and are incorporated by reference in) the disclosure of this application.

TECHNICAL FIELD

This document relates to methods and materials for using 4-aminopyridine (4-AP) and/or one or more derivatives of 4-AP. For example, a composition containing 4-AP and/or one or more derivatives of 4-AP can be administered (e.g., orally administered) to a mammal to increase a level of bone morphogenetic protein 2 (BMP-2) polypeptides within the mammal. For example, a composition containing 4-AP and/or one or more derivatives of 4-AP can be administered (e.g., orally administered) to a mammal having bone loss to treat the mammal.

BACKGROUND INFORMATION

BMP-2 polypeptides can stimulate the production of bone, and recombinant human protein (rhBMP-2) polypeptides are currently available for orthopedic and dental uses in the United States (Khan et al., *Expert Opin. Biol. Ther.*, 4(5):741-8 (2004); and Schliephake et al., *Clin. Oral Implants Res.*, 16(5):563-9 (2005)). However, current BMP-2 polypeptide therapies require invasive implantation of carriers and/or delivery systems that provide BMP-2 polypeptides (Agrawal et al., *J. Biomed. Mat. Res. Part B: Appl. Biomater.*, Early View (4):904-925 (2016)).

SUMMARY

This document provides methods and materials for using 4-AP and/or one or more derivatives of 4-AP. For example, a composition containing 4-AP and/or one or more derivatives of 4-AP can be administered (e.g., orally administered) to a mammal to increase a level of BMP-2 polypeptides within the mammal. For example, a composition containing 4-AP and/or one or more derivatives of 4-AP can be administered (e.g., orally administered) to a mammal having bone loss to increase the level of BMP-2 within the mammal, thereby treating the mammal's bone loss.

As demonstrated herein, administering a composition containing 4-AP and/or one or more derivatives of 4-AP to a mammal (e.g., a human) can increase BMP-2 expression within the mammal. For example, a composition containing 4-AP and/or one or more derivatives of 4-AP can be administered to a mammal (e.g., a human) having a disease, disorder, or condition characterized by a reduced level of one or more BMP-2 polypeptides (e.g., a disease, disorder, or condition associated with bone loss) to treat the mammal.

Having the ability to increase BMP-2 expression as described herein (e.g., by orally administering a composition containing 4-AP and/or one or more derivatives of 4-AP) provides a unique and unrealized opportunity to non-invasively increase a level of BMP-2 polypeptides (e.g., to treat a disease, disorder, or condition associated with bone loss) in a mammal.

In general, one aspect of this document features methods for increasing a level of a BMP-2 polypeptide in a mammal. The methods can include, or consist essentially of, administering a composition comprising 4-AP or one or more derivatives of 4-AP to a mammal. The mammal can be a human. The human can have been identified as being in need of increased BMP-2 polypeptide expression. The administering can include a systemic administration. The systemic administration can be an oral administration. The mammal can have a disease, disorder, or condition associated with reduced BMP-2 polypeptide expression. The disease, disorder, or condition associated with reduced BMP-2 polypeptide expression can include bone loss. The disease, disorder, or condition can be osteoporosis, a bone cancer, a bone fracture, a congenital bone disease, a degenerative bone disease, a dietary bone insufficiency, or an environmental exposure bone insufficiency.

In another aspect, this document features methods for treating a mammal having a disease, disorder, or condition associated with reduced BMP-2 polypeptide expression. The methods can include, or consist essentially of, administering a composition comprising 4-AP or one or more derivatives of 4-AP to mammal having a disease, disorder, or condition associated with reduced BMP-2 polypeptide expression; and detecting an increased level of a BMP-2 polypeptide in a sample obtained from the mammal. The increased level of the BMP-2 polypeptide can be a serum level that is greater than 10 pg/mL. The sample can be a urine, whole blood, serum, plasma, bone tissue, bone marrow, lymph, saliva, or cerebrospinal fluid (CSF) sample. The sample can be obtained at least 0.5 hours after the administering of the composition comprising 4-AP or one or more derivatives of 4-AP to the mammal. The mammal can be a human. The administering can include a systemic administration. The systemic administration can be oral administration. The human can have been identified as having the disease, disorder, or condition associated with reduced BMP-2 polypeptide expression. The disease, disorder, or condition associated with reduced BMP-2 polypeptide expression can include bone loss. The disease, disorder, or condition can be osteoporosis, a bone cancer, a bone fracture, a congenital bone disease, a degenerative bone disease, a dietary bone insufficiency, or an environmental exposure bone insufficiency.

In another aspect, this document features uses of a composition comprising 4-AP or one or more derivatives of 4-AP to increase BMP-2 polypeptide expression in a mammal. The mammal can be a human. The human can have been identified as being in need of increased BMP-2 polypeptide expression.

In another aspect, this document features compositions comprising 4-AP or one or more derivatives of 4-AP for use in the preparation of a medicament to increase BMP-2 polypeptide expression in a mammal. The mammal can be a human. The human can have been identified as being in need of increased BMP-2 polypeptide expression.

In another aspect, this document features compositions comprising 4-AP or one or more derivatives of 4-AP for use in increasing BMP-2 polypeptide expression in a mammal. The mammal can be a human. The human can have been identified as being in need of increased BMP-2 polypeptide expression.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2A: Representative image of a western blot of BMP-2 at day 3, 7, and 14. FIG. 2B: Densitometric analysis was carried out and the BMP-2 was normalized with GAPDH to calculate fold change. Data are presented as mean±SEM (n=3). Values are significant at *$p<0.05$, Abbreviations used; 4—AP-4-aminopyridine, BMP-2—bone morphogenetic protein-2, GAPDH-glyceraldehyde-3-phosphate dehydrogenase.

FIG. 4A: Representative X-ray images at the end of 21 days of 4-AP treatment. FIG. 4B: Representative micro-CT images of tibia fracture on day 21. FIG. 4C: Representative cross-sectional micro-CT images of the fracture show less mineralization in untreated. FIG. 4D: Graphical presentation of Micro CT analysis of bone mineral density (BMD), and bone volume density (BV/TV). Data are presented as mean±SEM (n=6). Values are significant at *$p<0.05$. Abbreviations used; 4-AP—4-aminopyridine.

DETAILED DESCRIPTION

Figure 1:
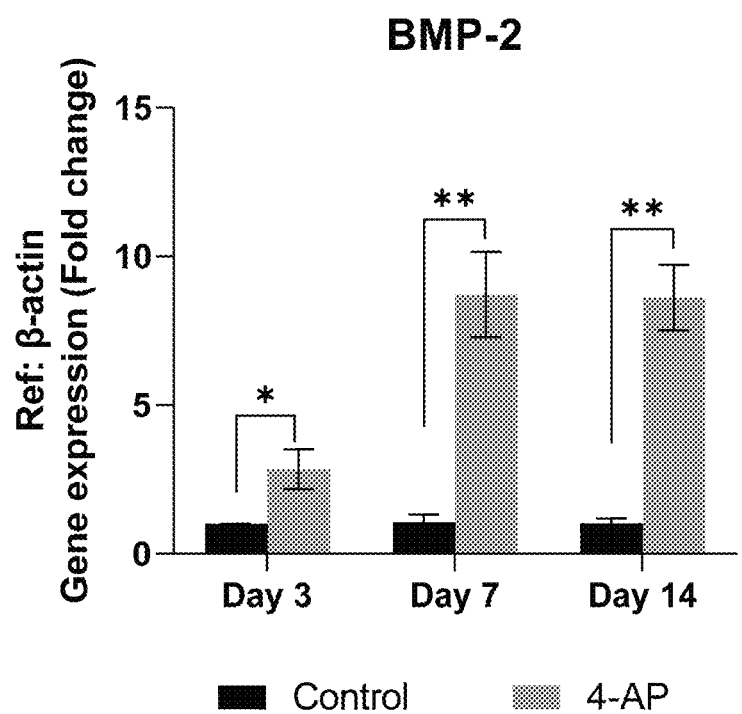
FIG. 1. 4-AP upregulates BMP-2 expression in human bone marrow mesenchymal stem cells (hBMSCs). hBMSCs were incubated in Dulbecco's modified Eagle's medium supplemented with 10% FBS and penicillin/streptomycin (100 U/mL penicillin and 100 mg/mL streptomycin) in the presence of 1000 µM 4-AP induced expression of BMP-2 gene. BMP-2 gene expression was increased at day 3 and remained high at day 7 and day 14. The gene expression levels of BMP-2 were normalized with β-actin and were then used to calculate fold change in 4-AP treated compared to control. Data are presented as mean±SEM (n=3). Values are significant at *$p<0.05$, **$p<0.01$. Abbreviations used; BMP-2 —bone morphogenetic protein-2.

This document provides methods and materials for using 4-AP and/or one or more derivatives of 4-AP. In some cases, this document provides methods and materials for increasing level of one or more BMP-2 polypeptides within a mammal (e.g., a human). For example, a composition containing 4-AP and/or one or more derivatives of 4-AP can be administered (e.g., orally administered) to a mammal to increase a level of BMP-2 polypeptides within the mammal. In some cases, this document provides methods and materials for treating a mammal (e.g., a human) identified as being in need of increased BMP-2 polypeptide expression (e.g., having a disease, disorder, or condition characterized by a reduced level of one or more BMP-2 polypeptides). For example, a composition containing 4-AP and/or one or more derivatives of 4-AP can be administered (e.g., orally administered) to a mammal having bone loss to increase the level of BMP-2 within the mammal, thereby treating the mammal's bone loss.

Any appropriate mammal can be treated as described herein. Examples of mammals that can be treated as described herein include, without limitation, humans, non-human primates such as monkeys, horses, bovine species, porcine species, dogs, cats, mice, rats, rabbits, and goats. In some cases, a human in need of increased BMP-2 polypeptide expression can be treated as described herein. In some cases, a human having bone loss (or identified as being likely to experience bone loss) can be treated as described herein. In some cases, the methods provided herein can be used to treat an animal that is not a mammal. For example, the methods provided herein can be used to increase a level of one or more BMP-2 polypeptides in a fowl (e.g., a chicken).

In some cases, a mammal (e.g., a human) to be treated as described herein (e.g., by administering a composition containing 4-AP and/or one or more derivatives of 4-AP) can have bone loss in one or more injured bones (e.g., can have injury-induced bone loss). For example, a mammal having nerve injury-induced bone loss can be treated by administering a composition containing 4-AP and/or one or more derivatives of 4-AP. For example, a mammal having muscle injury-induced bone loss can be treated by administering a composition containing 4-AP and/or one or more derivatives of 4-AP.

In some cases, a mammal (e.g., a human) to be treated as described herein (e.g., by administering a composition containing 4-AP and/or one or more derivatives of 4-AP) can have one or more diseases, disorders, or conditions associated with bone loss. Examples of diseases, disorders, and conditions associated with bone loss include, without limitation, osteoporosis, bone cancers, bone fractures (e.g., insufficiency fractures), congenital bone diseases, degenerative bone diseases, dietary bone insufficiencies, and environmental exposure bone insufficiencies (e.g., bone insufficiencies caused by toxic exposure such as lead poisoning).

In some cases, a mammal (e.g., a human) to be treated as described herein (e.g., by administering a composition containing 4-AP and/or one or more derivatives of 4-AP) can be in need of bone fusion. For example, a human who has been identified as being in need of bone fusion (e.g., a mammal having one or more bone fractures) can be treated as described herein (e.g., by administering a composition containing 4-AP and/or one or more derivatives of 4-AP).

In some cases, a mammal (e.g., a human) having bone loss (or identified as being likely to experience bone loss) that lacks bone fractures can be treated as described herein (e.g., by administering a composition containing 4-AP and/or one or more derivatives of 4-AP). For example, a human with no current bone fractures who has been identified as having bone loss can be treated as described herein (e.g., by administering a composition containing 4-AP and/or one or more derivatives of 4-AP).

In some cases, a composition containing 4-AP and/or one or more derivatives of 4-AP can be administered (e.g., orally administered) to a mammal (e.g., a human such as a human identified as being in need of increased BMP-2 polypeptide expression) to increase a level of one or more BMP-2 polypeptides within the mammal. For example, a composition containing 4-AP and/or one or more derivatives of 4-AP can be administered (e.g., orally administered) to a mammal (e.g., a human) in need thereof (e.g., a mammal identified as being in need of increased BMP-2 polypeptide expression) to increase expression of one or more BMP-2 polypeptides in cells within the mammal. The term "increased level" as used herein with respect to a level of a BMP-2 polypeptide in a mammal refers to any level that is greater than the level of that BMP-2 polypeptide observed in that mammal prior to being treated as described herein (e.g., prior to being administered a composition containing 4-AP and/or one or more derivatives of 4-AP). In some cases, an increased level of a BMP-2 polypeptide can be a level that is at least 5 percent (e.g., at least 10, at least 15, at least 20, at least 25, at least 35, at least 50, at least 75, at least 100, or at least 150 percent) greater than the level of that BMP-2 polypeptide prior to being treated as described herein. In some cases, an increased level of a BMP-2 polypeptide can be a serum level that is greater than 10 pg/mL in a human. In some cases, when samples have an undetectable level of a BMP-2 polypeptide prior to treatment as described herein, an increased level can be any detectable level of a BMP-2 polypeptide. It will be appreciated that levels from comparable samples are used when determining whether or not a particular level is an increased level.

When the methods and materials described herein are used to increase a level of one or more BMP-2 polypeptides within a mammal (e.g., a human such as a human identified as being in need of increased BMP-2 polypeptide expression), a level of any appropriate BMP-2 polypeptide can be increased. Examples of BMP-2 polypeptides that can be increased as described herein include, without limitation, BMP-2 polypeptides having an amino acid sequence set forth in any one of National Center for Biotechnology Information (NCBI) GenBank® or GenPept® Accession No. P12643, a fragment of this amino acid sequence (e.g., as in an amino acid sequence including amino acids 283-396 of the sequence set forth as Accession No. P12643), or a homodimer of the fragment (e.g., a disulfide-linked homodimer in which each monomer of the homodimer includes an amino acid sequence having amino acids 283-396 of the sequence set forth as Accession No. P12643). BMP-2 polypeptides can be used in any form for the methods herein, such as pro-peptide forms, cleaved or mature forms, or dimerized forms, as may be present in a sample obtained from a mammal.

When a composition containing 4-AP and/or one or more derivatives of 4-AP is administered (e.g., orally administered) to a mammal (e.g., a human) identified as being in need of increased BMP-2 polypeptide expression, the mammal can have a disease, disorder, or condition characterized by a reduced level of one or more BMP-2 polypeptides. In some cases, a reduced level of BMP-2 polypeptide can refer to a level that is less than 10 pg/mL in a human. In some cases, a mammal having a disease, disorder, or condition characterized by a reduced level of one or more BMP-2 polypeptides can have bone loss (or can be identified as being likely to experience bone loss). Examples of diseases, disorders, and conditions that are characterized by a reduced level of one or more BMP-2 polypeptides and can be treated as described herein (e.g., by administering a composition containing 4-AP and/or one or more derivatives of 4-AP) include, without limitation, osteoporosis, bone cancers, bone fractures (e.g., insufficiency fractures), congenital bone diseases, degenerative bone diseases, dietary bone insufficiencies, and environmental exposure bone insufficiencies (e.g., bone insufficiencies caused by toxic exposure such as lead poisoning).

In some cases, methods described herein also can include identifying the mammal as having a disease, disorder, or condition characterized by a reduced level of one or more BMP-2 polypeptides. Examples of methods for identifying a mammal as having a disease, disorder, or condition characterized by a reduced level of one or more BMP-2 polypeptides include, without limitation, detecting a level of one or more BMP-2 polypeptides in a sample obtained from the mammal or identifying the mammal as having bone loss. Examples of methods for identifying a mammal as having bone loss include, without limitation, bone density tests and imaging techniques (e.g., X-rays, bone densitometry, micro-computed tomography (microCT), and ultrasound), and mechanical testing to determine the proportion of mineral in bones. Once identified as having a disease, disorder, or condition characterized by a reduced level of one or more BMP-2 polypeptides, the mammal can be administered or instructed to self-administer a composition described herein (e.g., a composition containing 4-AP and/or one or more derivatives of 4-AP).

In some cases, methods described herein also can include detecting a level of one or more BMP-2 polypeptides in a sample obtained from a mammal (e.g., a human). For example, a level of one or more BMP-2 polypeptides can be detected in a sample obtained from a mammal (e.g., a human) that has been administered a composition described herein (e.g., a composition containing 4-AP and/or one or more derivatives of 4-AP) before or after (or both before and after) that composition was administered to the mammal.

Any appropriate sample can be obtained from a mammal (e.g., a human) to detect a level of expression of one or more BMP-2 polypeptides. In some cases, a sample can be a biological sample. In some cases, a sample can contain one or more biological molecules (e.g., nucleic acids such as DNA and RNA, polypeptides, carbohydrates, lipids, hormones, and/or metabolites). In some cases, a sample can be a fluid sample. In some cases, a sample can be a tissue sample. Examples of samples that can be assessed as described herein include, without limitation, urine, whole blood, serum, plasma, bone tissue, bone marrow, lymph, saliva, and cerebrospinal fluid (CSF). A biological sample can be a fresh sample or a fixed sample (e.g., a formaldehyde-fixed sample or a formalin-fixed sample). In some cases, a biological sample can be a processed sample (e.g., to isolate or extract one or more biological molecules). In some cases, a sample can be from a mammal (e.g., a human) to be treated as described herein. In some cases, a sample can be from a mammal (e.g., a human) that is genetically related to a mammal to be treated as described herein.

Any appropriate method can be used to detect a level of expression of one or more BMP-2 polypeptides within a sample (e.g., a sample obtained from a mammal such as a human). In some cases, a level of expression of one or more BMP-2 polypeptides within a sample can be determined by detecting a level of one or more BMP-2 polypeptides in the sample. For example, immunoassays (e.g., immunohistochemistry (IHC) techniques, western blotting techniques, and enzyme-linked immunoassay (ELISA) assays) and mass spectrometry (MS) techniques (e.g., proteomics-based MS assays, targeted quantification-based MS assays, and mass spectrometry techniques including high performance liquid chromatography (HPLC-MS)) can be used to determine a level of one or more BMP-2 polypeptides in a sample. When an immunoassay is used to determine a level of one or more BMP-2 polypeptides in a sample, the immunoassay can use any appropriate antibody. Examples of antibodies that can be used in an immunoassay to determine a level of one or more BMP-2 polypeptides in a sample include, without limitation, human BMP-2 antibody MAB3551 (R&D systems) and EPR20807 (Abcam #ab214821). In some cases, a level of expression of one or more BMP-2 polypeptides within a sample can be determined by detecting a level of mRNA encoding a BMP-2 polypeptide in the sample. For example, polymerase chain reaction (PCR)-based techniques such as quantitative reverse transcription (RT)-PCR (qPCR) techniques, in situ hybridization techniques, northern blot assays, nuclease protection assays, and microarrays can be used to determine a level of mRNA encoding a BMP-2 polypeptide in a sample.

A sample can be obtained from a mammal (e.g., a human) at any time. In some cases, a sample can be obtained from a mammal before or after (or both before and after) the mammal has been administered a composition described herein (e.g., a composition containing 4-AP and/or one or more derivatives of 4-AP). For example, a sample can be obtained from mammal (e.g., a human) within 72 hours of the mammal having been administered a composition described herein (e.g., a composition containing 4-AP and/or one or more derivatives of 4-AP). For example, a sample can be obtained from mammal (e.g., a human) at least 0.5 hours after the mammal has been administered a composition described herein (e.g., a composition containing 4-AP and/or one or more derivatives of 4-AP).

In certain instances, a level of one or more BMP-2 polypeptides within a mammal (e.g., within a sample obtained from a mammal) can be detected at different time points over a course of a treatment with a composition described herein (e.g., a composition containing 4-AP and/or one or more derivatives of 4-AP). For example, two or more (e.g., two, three, four, five, six, or more) samples can be obtained from a mammal at different time point over the course of treatment.

A composition described herein (e.g., a composition containing 4-AP and/or one or more derivatives of 4-AP) can be administered (e.g., orally administered) to a mammal (e.g., a human) identified as being in need of increased BMP-2 polypeptide expression, to increase a level of one or more BMP-2 polypeptides in any type of bone. In some cases, the methods and materials provided herein can be used to increase a level of one or more BMP-2 polypeptides in cortical bone. In some cases, the methods and materials provided herein can be used to increase a level of one or more BMP-2 polypeptides in cancellous bone. Examples of types of bones that can be affected by a disease, disorder, or condition characterized by a reduced level of one or more BMP-2 polypeptides and can be treated as described herein include, without limitation, long bones, short bones, flat bones, irregular bones, sesamoid bones, and ossifications.

A composition described herein (e.g., a composition containing 4-AP and/or one or more derivatives of 4-AP) can be administered (e.g., orally administered) to a mammal (e.g., a human) identified as being in need of increased BMP-2 polypeptide expression, to increase a level of one or more BMP-2 polypeptides in any bone within a mammal (e.g., a bone in any location within a mammal). In some cases, the methods and materials provided herein can be used to increase a level of one or more BMP-2 polypeptides in the spine of a mammal. In some cases, the methods and materials provided herein can be used to increase a level of one or more BMP-2 polypeptides in an arm of a mammal. In some cases, the methods and materials provided herein can be used to increase a level of one or more BMP-2 polypeptides in a leg of a mammal.

A composition described herein (e.g., a composition containing 4-AP and/or one or more derivatives of 4-AP) can include 4-AP and/or any appropriate derivative(s) of 4-AP. Examples of derivatives of 4-AP that can be included in a composition described herein include, without limitation, 3,4-diaminopyridine, 3-hydroxy-4-aminopyridine, N-(4-pyridyl)-t-butyl carbamate, N-(4-pyridyl) ethyl carbamate, N-(4-pyridyl) methyl carbamate, and N-(4-pyridyl) isopropyl carbamate. In some cases, 4-AP and/or one or more derivatives of 4-AP can have a structure according to Formula I:

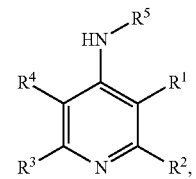

where $R^1$, $R^2$, $R^3$, $R^4$, and $R^5$ are each independently selected from hydrogen (H), halogen (e.g., fluorine (F), chlorine (Cl), bromine (Br) or iodine (I)), amine, hydroxyl (e.g., —OH), alkoxy (e.g., —OAk), carboxyl (e.g., —CO$_2$H), alkoxycarbonyl (e.g., —C(O)—OAk), or alkyl (e.g., $C_{1-6}$ alkyl or Ak). For example, $R^1$, $R^2$, $R^3$, $R^4$, and $R^5$ can all be hydrogen. Examples of amine include —NR$^{N1}$R$^{N2}$, in which each of R$^{N1}$ and R$^{N2}$ is, independently, H or optionally substituted alkyl, or R$^{N1}$ and R$^{N2}$, taken together with the nitrogen atom to which each are attached, form a heterocyclyl group. Examples of alkyl or Ak include a branched or unbranched saturated hydrocarbon group of 1 to 24 carbon atoms ($C_{1-24}$), such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. Substitutions for alkyl can include a halogen (e.g., any herein), hydroxyl, alkoxy, carboxyl, or amine.

In some cases, 4-AP or a derivative thereof can be a potassium channel blocker. In some cases, 4-AP or a derivative thereof can be a calcium channel agonist. In some cases, 4-AP or a derivative thereof can be electrically active. In some cases, 4-AP or a derivative thereof can be in the form of a free base. In some cases, 4-AP or a derivative thereof can be in the form of a salt (e.g., pharmaceutically acceptable salt). When 4-AP or a derivative thereof is in the form of a salt, the salt can include any appropriate acid (e.g., an organic acid or an inorganic acid). Examples of acids that can be used to form a salt with 4-AP or a derivative thereof include, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid.

In some cases, 4-AP and/or one or more derivatives of 4-AP can be as described elsewhere (see, e.g., U.S. Patent Application Publication No. 2018/0271847, U.S. Pat. No. 9,993,429, and International Patent Application Publication WO 2021/150773).

A composition described herein (e.g., a composition containing 4-AP and/or one or more derivatives of 4-AP) can include any appropriate amount of 4-AP and/or one or more derivatives of 4-AP. In some cases, a composition described herein can include from about 0.1 µM to about 150 µM (e.g., from about 0.1 µM to about 125 µM, from about 0.1 µM to about 100 µM, from about 0.1 µM to about 75 µM, from about 0.1 µM to about 50 µM, from about 0.1 µM to about 30 µM, from about 0.1 µM to about 20 µM, from about 0.1 µM to about 10 µM, from about 0.1 µM to about 5 µM, from about 0.1 µM to about 1 µM, from about 1 µM to about 150 µM, from about 5 µM to about 150 µM, from about 10 µM to about 150 µM, from about 20 µM to about 150 µM, from about 30 µM to about 150 µM, from about 50 µM to about 150 µM, from about 75 µM to about 150 µM, from about 100 µM to about 150 µM, from about 125 µM to about 150 µM, from about 1 µM to about 125 µM, from about 5 µM to about 100 µM, from about 10 µM to about 75 µM, from about 25 µM to about 50 µM, from about 5 µM to about 25 µM, from about 25 µM to about 50 µM, from about 50 µM about 75 µM, from about 75 µM to about 100 µM, or from about 100 µM to about 125 µM) of 4-AP and/or one or more derivatives of 4-AP. In some cases, a composition described herein can include from about 0.01% to about 99% (e.g., from about 0.01% to about 90%, from about 0.01% to about 80%, from about 0.01% to about 70%, from about 0.01% to about 60%, from about 0.01% to about 50%, from about 0.01% to about 40%, from about 0.01% to about 30%, from about 0.01% to about 20%, from about 0.01% to about 10%, from about 0.01% to about 5%, from about 0.01% to about 1%, from about 1% to about 99%, from about 5% to about 99%, from about 10% to about 99%, from about 20% to about 99%, from about 30% to about 99%, from about 40% to about 99%, from about 50% to about 99%, from about 60% to about 99%, from about 70% to about 99%, from about 80% to about 99%, from about 90% to about 99%, from about 10% to about 90%, from about 20% to about 80%, from about 30% to about 70%, from about 40% to about 60%, from about 10% to about 30%, from about 30% to about 50%, from about 50% to about 70%, or from about 70% to about 90%) of 4-AP and/or one or more derivatives of 4-AP.

In some cases, a composition described herein (e.g., a composition containing 4-AP and/or one or more derivatives of 4-AP) can include one or more pharmaceutically acceptable carriers (additives), excipients, and/or diluents. Examples of pharmaceutically acceptable carriers, excipients, and diluents that can be used in a composition described herein include, without limitation, saline (e.g., phosphate-buffered saline (PBS)), sucrose, lactose, starch (e.g., starch glycolate), cellulose, cellulose derivatives (e.g., modified celluloses such as microcrystalline cellulose and cellulose ethers like hydroxypropyl cellulose (HPC) and cellulose ether hydroxypropyl methylcellulose (HPMC)), xylitol, sorbitol, mannitol, gelatin, polymers (e.g., poly (lactic-co-glycolic acid), polyethylene glycol, polyvinylpyrrolidone (PVP), crosslinked polyvinylpyrrolidone (crospovidone), carboxymethyl cellulose, polyethylene-polyoxypropylene-block polymers, and crosslinked sodium carboxymethyl cellulose (croscarmellose sodium)), titanium oxide, azo dyes, silica gel, fumed silica, talc, magnesium carbonate, vegetable stearin, magnesium stearate, aluminum stearate, stearic acid, antioxidants (e.g., vitamin A, vitamin E, vitamin C, retinyl palmitate, and selenium), citric acid, sodium citrate, parabens (e.g., methyl paraben and propyl paraben), petrolatum, dimethyl sulfoxide, mineral oil, serum proteins (e.g., human serum albumin), glycine, sorbic acid, potassium sorbate, water, salts or electrolytes (e.g., saline, protamine sulfate, disodium hydrogen phosphate, potassium hydrogen phosphate, sodium chloride, and zinc salts), colloidal silica, magnesium trisilicate, polyacrylates, waxes, wool fat, and lecithin.

A composition described herein (e.g., a composition containing 4-AP and/or one or more derivatives of 4-AP) can be administered to a mammal in need thereof (e.g., a mammal having bone loss) locally or systemically. In some cases, a compositions described herein can be administered locally. For example, a composition described herein can be administered locally by injection directly into, around, and/or near an area of bone loss on a mammal (e.g., a human). In some cases, a composition described herein can be administered systemically. For example, a composition described herein can be designed for oral or parenteral (including intraperitoneal, subcutaneous, intramuscular, intravenous, and intradermal) administration to a mammal having bone loss. Compositions suitable for oral administration include, without limitation, liquids, tablets, capsules, pills, powders, gels, and granules. Compositions suitable for parenteral administration include, without limitation, aqueous and non-aqueous sterile injection solutions that can contain anti-oxidants, buffers, bacteriostats, and solutes that render the formulation isotonic with the blood of the intended recipient. In some cases, a composition described herein can be formulated for parenteral administration (e.g., intraperitoneal injection or intravenous injection).

Any appropriate amount can be administered to a mammal to treat the mammal as described herein. For example, an effective amount of 4-AP and/or one or more derivatives of 4-AP that can be administered to a mammal (e.g., a human) can be any amount that increases a level of one or more BMP-2 polypeptides (e.g., can treat a disease, disorder, or condition characterized by a reduced level of one or more BMP-2 polypeptides such as bone loss) in a mammal without producing significant toxicity to the mammal. In some cases, an effective amount of 4-AP and/or one or more derivatives of 4-AP can be from about 0.05 milligrams per kilogram body weight (mg/kg) to about 1 mg/kg (e.g., from about 0.05 mg/kg to about 0.9 mg/kg, from about 0.05 mg/kg to about 0.8 mg/kg, from about 0.05 mg/kg to about 0.7 mg/kg, from about 0.05 mg/kg to about 0.6 mg/kg, from about 0.05 mg/kg to about 0.5 mg/kg, from about 0.05 mg/kg to about 0.4 mg/kg, from about 0.05 mg/kg to about 0.3 mg/kg, from about 0.05 mg/kg to about 0.2 mg/kg, from about 0.05 mg/kg to about 0.1 mg/kg, from about 0.1 mg/kg to about 1 mg/kg, from about 0.2 mg/kg to about 1 mg/kg, from about 0.3 mg/kg to about 1 mg/kg, from about 0.4 mg/kg to about 1 mg/kg, from about 0.5 mg/kg to about 1 mg/kg, from about 0.6 mg/kg to about 1 mg/kg, from about 0.7 mg/kg to about 1 mg/kg, from about 0.8 mg/kg to about 1 mg/kg, from about 0.9 mg/kg to about 1 mg/kg, from about 0.1 mg/kg to about 0.9 mg/kg, from about 0.2 mg/kg to about 0.8 mg/kg, from about 0.3 mg/kg to about 0.7 mg/kg, from about 0.4 mg/kg to about 0.6 mg/kg, from about 0.1 mg/kg to about 0.3 mg/kg, from about 0.2 mg/kg to about 0.4 mg/kg, from about 0.3 mg/kg to about 0.5 mg/kg, from about 0.4 mg/kg to about 0.6 mg/kg, from about 0.5 mg/kg to about 0.7 mg/kg, from about 0.6 mg/kg to about 0.8 mg/kg, or from about 0.7 mg/kg to about 0.9 mg/kg). The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the disease, disorder, or condition characterized by a reduced level of one or more BMP-2 polypeptides (e.g., bone loss) may require an increase or decrease in the actual effective amount administered.

The frequency of administration of a composition described herein (e.g., a composition containing 4-AP and/or one or more derivatives of 4-AP) can be any frequency that increases a level of one or more BMP-2 polypeptides (e.g., can treat a disease, disorder, or condition characterized by a reduced level of one or more BMP-2 polypeptides such as bone loss) in a mammal without producing significant toxicity to the mammal. For example, the frequency of administration can be from about once a day to about once a week, from about once a week to about once every two months, from about once every two weeks to about once every six weeks, or from about once every three weeks to about once a month (e.g., once every four weeks). The frequency of administration can remain constant or can be variable during the duration of treatment. A course of treatment with a composition described herein can include rest periods. For example, a composition described herein can be administered once a month over a six-month period followed by a rest period (e.g., a one or two month rest period), and such a regimen can be repeated multiple times. As with the effective amount, various factors can influence the actual frequency of administration used for a particular application. For example, the effective amount, duration of treatment, use of multiple treatment agents, route of administration, and severity of the bone loss may require an increase or decrease in administration frequency.

An effective duration for administering a composition described herein (e.g., a composition containing 4-AP and/or one or more derivatives of 4-AP) can be any duration that increases a level of one or more BMP-2 polypeptides (e.g., can treat a disease, disorder, or condition characterized by a reduced level of one or more BMP-2 polypeptides such as bone loss) in a mammal without producing significant toxicity to the mammal. For example, the effective duration can vary from several days to several weeks, months, or years. In some cases, the effective duration for the treatment of bone loss can range in duration from about one month to about 6 months. Multiple factors can influence the actual effective duration used for a particular treatment. For example, an effective duration can vary with the frequency of administration, effective amount, use of multiple treatment agents, route of administration, and severity of the bone loss being treated.

In some cases, the methods and materials described herein can be used as the sole active agent used to increase a level of one or more BMP-2 polypeptides in a mammal (e.g., to treat a mammal such as a human having a disease, disorder, or condition characterized by a reduced level of one or more BMP-2 polypeptides such as bone loss). For example, a composition containing 4-AP and/or one or more derivatives of 4-AP can be used as the sole active agent(s) used to increase a level of one or more BMP-2 polypeptides in a mammal (e.g., a human).

In some cases, methods described herein also can include administering to a mammal (e.g., a human) identified as having a disease, disorder, or condition characterized by a reduced level of one or more BMP-2 polypeptides (e.g., identified as having bone loss or as being likely to experience bone loss) one or more (e.g., one, two, three, four, five or more) additional agents used to increase a level of one or more BMP-2 polypeptides and/or to treat bone loss in addition to a composition described herein (e.g., a composition containing 4-AP and/or one or more derivatives of 4-AP). Examples of agents that can be used to increase a level of one or more BMP-2 polypeptides include, without limitation, recombinant BMP-2 polypeptides such as recombinant human protein (rhBMP-2). Examples of agents that can be used to treat bone loss include, without limitation, alendronate (e.g., BINOSTO® and FOSAMAX®), risedronate (e.g., ACTONEL® and ATELVIA®), ibandronate (e.g., BONIVA®), zoledronic acid (e.g., RECLAST® and ZOMETA®), denosumab (e.g., PROLIA® and XGEVA®), estrogen, raloxifene (e.g., EVISTA®), teriparatide (e.g., FORTEO®), abaloparatide (e.g., TYMLOS®), and romosozumab (EVENITY®). In cases where a mammal having a disease, disorder, or condition characterized by a reduced level of one or more BMP-2 polypeptides (e.g., bone loss) is treated with a composition described herein and is treated with one or more additional agents used to increase a level of one or more BMP-2 polypeptides and/or to treat bone loss, the additional agent(s) can be administered at the same time or independently. For example, the additional agent(s) can be formulated into a composition containing 4-AP and/or one or more derivatives of 4-AP to form a single composition. In some cases, a composition described herein can be administered first, and the one or more additional agents administered second, or vice versa.

The invention will be further described in the following examples, which do not limit the scope of the invention described in the claims.

EXAMPLES

Example 1: 4-AP and BMP-2 Expression in Human Bone Marrow Mesenchymal Stem Cells Human bone marrow mesenchymal stem cells (hBMSC) were cultured in growth medium supplemented with 4-AP for 3, 7, and 14 days. Total RNA was isolated from the cells at the end of treatment, converted to cDNA, and the gene expression of bone morphogenetic protein-2 (BMP-2) was analyzed by quantitative real-time PCR.

Gene expression by quantitative real-time PCR: Quantitative real-time PCR was carried out to determine gene expression of BMP-2 by hBMSCs incubated in Dulbecco's modified Eagle's medium with 10% fetal bovine serum (FBS) and penicillin/streptomycin (100 U/mL penicillin and 100 mg/mL streptomycin) at a humidified atmosphere of 5% $CO_2$ under 37° C. Cell cultures were supplemented with 1000 μM 4-AP for 3, 7, and 14 days. Total RNA was isolated from the cells and converted to cDNA using verso cDNA synthesis kit (Thermo Fischer Scientific). The cDNA obtained was analyzed in a quantitative real-time PCR (FIG. 1).

Figure 2A:
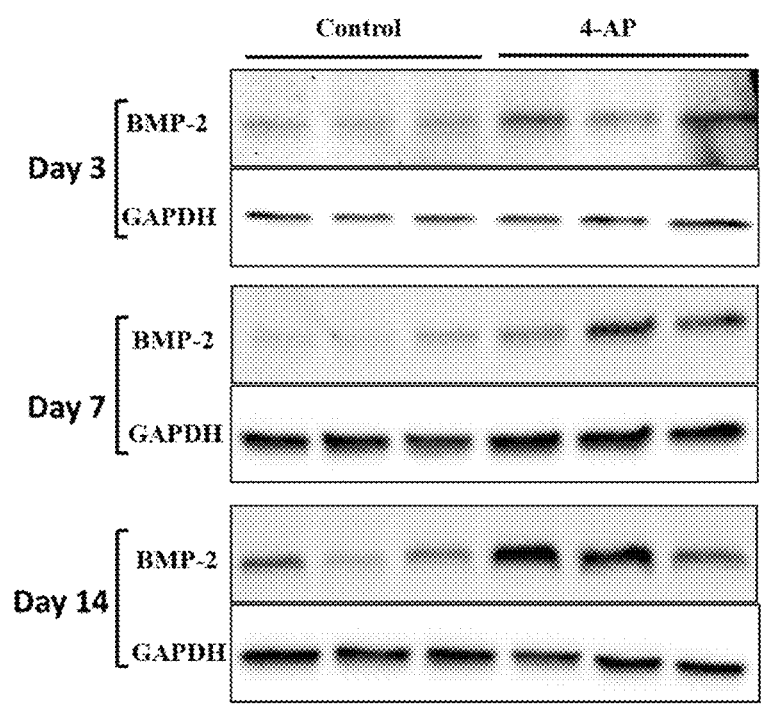
FIGS. 2A-2B. Western blot analysis of BMP-2 protein. Incubation of hBMSCs in Dulbecco's modified Eagle's medium supplemented with 10% FBS and penicillin/streptomycin (100 U/mL penicillin and 100 mg/mL streptomycin) in the presence of 1000 µM 4-AP increased BMP-2 protein at day 3, 7, and 14. The blots were stripped and reprobed with anti-GAPDH antibody.
Figure 2B:
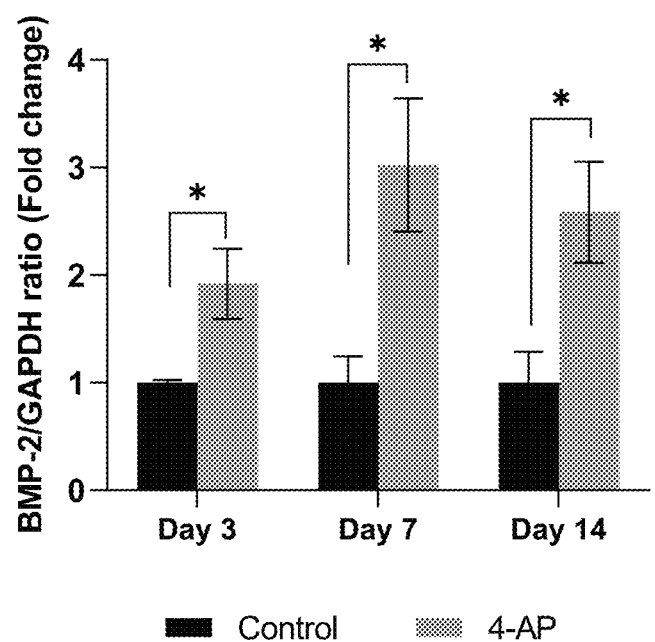

Protein level by western blot: Total protein was extracted from hBMSCs with RIPA lysis buffer at the end of 3, 7, and 14 days of 4-AP treatment. The protein concentrations of cell lysates were determined using Pierce BCA Protein Assay kit (Thermo Fischer Scientific). Total cell lysates containing equal amounts of protein were denatured with SDS reducing buffer. The denatured proteins were separated on 10% polyacrylamide gel and transferred to a PVDF membrane. The blots were blocked and probed with primary and secondary antibodies, followed by visualization of bands by chemiluminescence peroxidase substrate. The BMP-2 band intensities were analyzed by ImageJ software (FIGS. 2A and 2B).

These results demonstrate that a composition containing 4-AP and/or one or more derivatives of 4-AP can be administered to a mammal (e.g., a human) to increase a level of BMP-2 polypeptides within the mammal, thereby having the ability to treat bone loss, strengthen bone, and promote bone healing within a mammal.

Example 2: 4-AP and BMP-2 Expression in Human Fetal Osteoblasts

Figure 3:
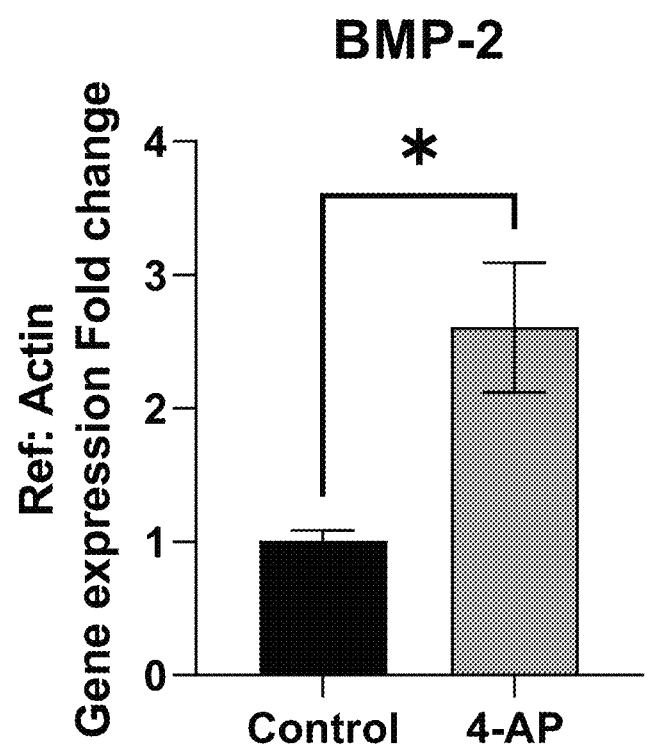
FIG. 3. 4-AP upregulates BMP-2 gene expression in human fetal osteoblasts (hFOB). PCR analysis revealed that hFOB treated with 4-AP significantly increased the expression of BMP-2 compared with the control group. hFOB were incubated in Dulbecco's modified Eagle's medium supplemented with 10% FBS and penicillin/streptomycin (100 U/ml penicillin and 100 mg/ml streptomycin) in presence of 1000 µM 4-AP for 3 days induced expression of genes. The gene expression levels were normalized with β-actin and was then used to calculate fold change in 4-AP treated compared to control. Data are presented as mean±SEM (n=3). Values are significant at *$p<0.05$. Abbreviations used; 4-AP—4-aminopyridine.
Figure 4A:
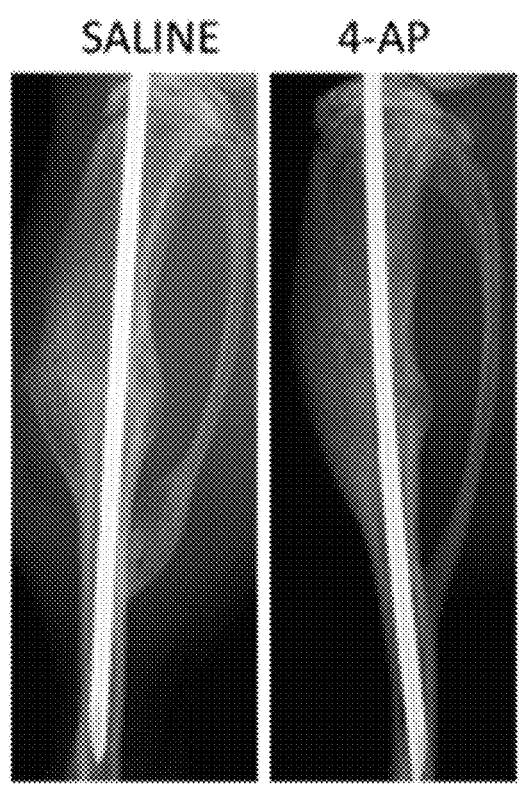
FIGS. 4A-4D. 4-AP enhanced bone fracture healing mice. 8 week old C57Bl/6J mice were subjected to mid-diaphysis tibial fracture, treated with 4-AP for 21 days, and harvested.
Figure 4B:
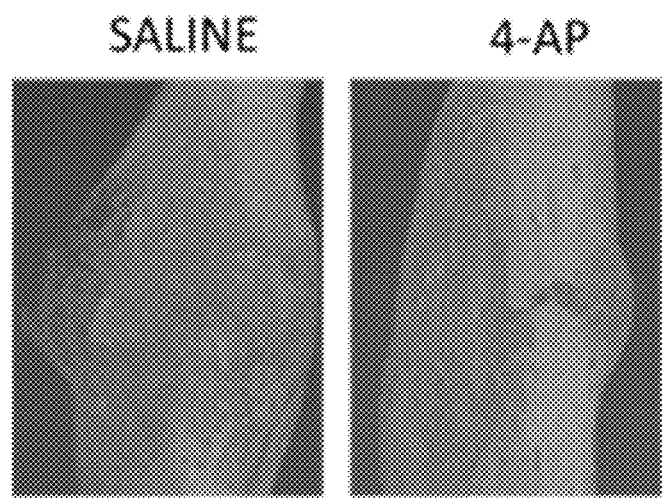
Figure 4C:
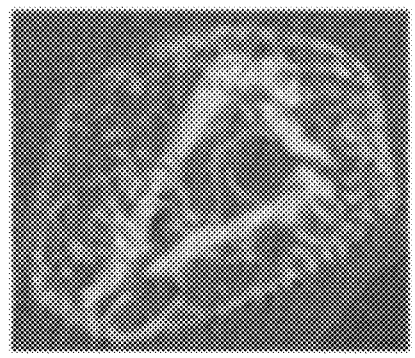
Figure 4C:
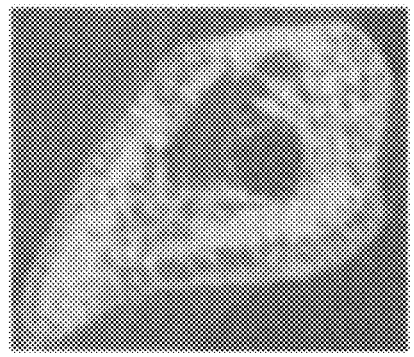
Figure 4D:
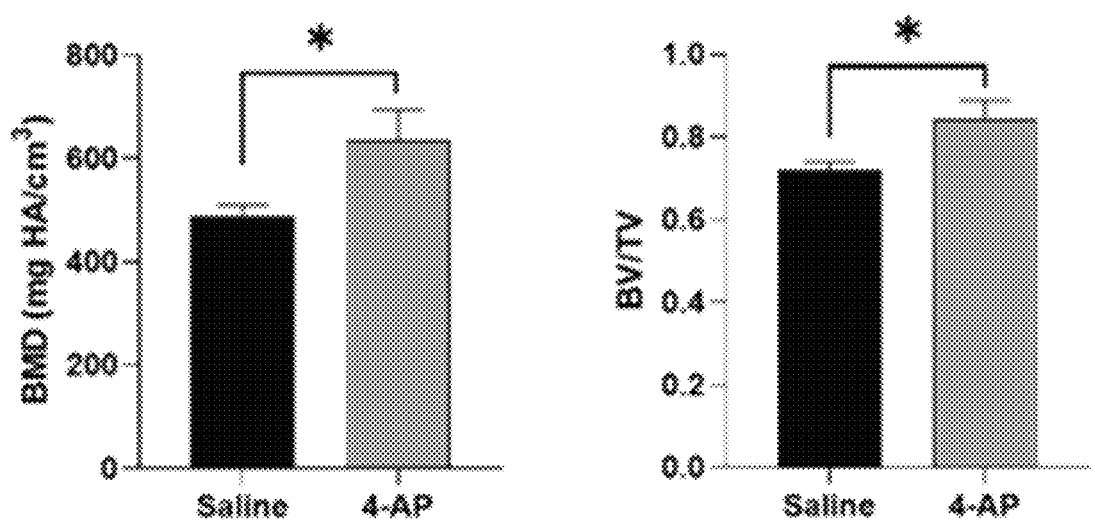

Human fetal osteoblasts (hFOB) were cultured in growth medium supplemented with 4-AP for 3 days. Total RNA was isolated from the cells at the end of treatment, converted to cDNA, and the gene expression of bone morphogenetic protein-2 (BMP-2) was analyzed by quantitative real-time PCR (FIG. 3).

These results demonstrate that a composition containing 4-AP and/or one or more derivatives of 4-AP can be administered to a mammal (e.g., a human) to increase a level of BMP-2 polypeptides within the mammal, thereby having the ability to treat bone loss, strengthen bone, and promote bone healing within a mammal.

Example 3: 4-AP and Bone Mineral Density in Animal Models

Ten-week-old male C57/BL6J mice were purchased from the Jackson laboratory (Bar Harbor, ME, USA) and were maintained in a 12-h light, 12-h dark cycle at 21.1° C. to 22.8° C. After acclimatization, all mice were randomly divided in to two groups: 1) control and 2) 4-AP.

A mid diaphysis tibial fracture was performed in ten-week-old male mice. After the mice were anesthetized with ketamine/xylazine, a 5 mm longitudinal incision will be made at the front of the proximal tibia. The mid diaphysis of the tibia will be identified, and an osteotomy will be created with a No. 11 scalpel blade preventing any comminution. A 27G hypodermic needle will be introduced into the tibial canal for intramedullary fixation. Buprenorphine was given as post-operative analgesia. X-ray images were acquired post-operatively and mice received saline or 4-AP on the same day. Control group received 100 µl of saline, and a 4-AP group received 40 µg/mouse/daily 4-AP (1.6 mg/kg) in saline intraperitoneally until day 21 post-surgery.

For micro-CT analysis, tibia of control and 4-AP mice were dissected of soft tissue and fixed in neutral buffered formalin. µCT scanning was conducted using a Scanco vivaCT 40. For callus analysis, tibia was scanned for a region spanning from femoral condyle growth plate to 3 mm distal from the callus center. Callus area from control and 4-AP mice tibia were assessed for bone mineral density (BMD) and percent bone volume per total volume (% BV/TV).

Tibial fracture was performed in C57BL/6J mice, which were then treated with 4-AP for 21 days for the evaluation of fracture healing parameters. The bone mineral density and bone volume density were determined by micro-CT analysis at the end of 21 days 4-AP treatment. The results showed a higher bone mineral density and bone volume density within the callus area of 4-AP treated mice compared to saline treated controls (FIGS. 4A to 4D).

These results demonstrate that a composition containing 4-AP and/or one or more derivatives of 4-AP can be administered to a mammal (e.g., a human) to increase a level of BMP-2 polypeptides within the mammal, thereby having the ability to treat bone loss, strengthen bone, and promote bone healing within a mammal.

Example 4: Increasing BMP-2 Polypeptide Expression

A human in need of treatment of a disease, disorder, or condition associated with reduced BMP-2 polypeptides is administered or self-administers a composition containing 4-AP and/or one or more derivatives of 4-AP. The administered composition containing 4-AP and/or one or more derivatives of 4-AP can increase a level of one or more BMP-2 polypeptides in the human (e.g., can increase BMP-2 polypeptide expression by cells within the human).

Example 5: Treating Bone Loss

A human identified as having bone loss (e.g., bone loss associated with a reduced BMP-2 polypeptides) is administered or self-administers a composition containing 4-AP and/or one or more derivatives of 4-AP. The administered composition containing 4-AP and/or one or more derivatives of 4-AP can treat the bone loss. In some cases, the administered composition containing 4-AP and/or one or more derivatives of 4-AP can increase the bone mineral density (BMD) of one or more bones within the mammal. In some cases, the administered composition containing 4-AP and/or one or more derivatives of 4-AP can increase the bone mineral content (BMC) of one or more bones within the mammal.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having osteoporosis, a bone cancer, a congenital bone disease, a degenerative bone disease, a dietary bone insufficiency, or an environmental exposure bone insufficiency, wherein said method comprises:
   (a) administering a composition comprising 4-aminopyridine (4-AP), 3,4-diaminopyridine, 3-hydroxy-4-aminopyridine, N-(4-pyridyl)-t-butyl carbamate, N-(4-pyridyl) ethyl carbamate, N-(4-pyridyl) methyl carbamate, N-(4-pyridyl) isopropyl carbamate, or a pharmaceutically acceptable salt thereof to said mammal, wherein said administering comprises a systemic administration; and
   (b) detecting an increased level of a BMP-2 polypeptide in a sample obtained from said mammal.

2. The method of claim 1, wherein said increased level of said BMP-2 polypeptide comprises a serum level that is greater than 10 pg/mL.

3. The method of claim 1, wherein said sample is selected from the group consisting of urine, whole blood, serum, plasma, bone tissue, bone marrow, lymph, saliva, and cerebrospinal fluid (CSF) samples.

4. The method of claim 1, wherein said sample is obtained at least 0.5 hours after said administering of said composition to said mammal.

5. The method of claim 1, wherein said mammal is a human.

6. The method of claim 5, wherein said human is identified as having said osteoporosis, said bone cancer, said congenital bone disease, said degenerative bone disease, said dietary bone insufficiency, or said environmental exposure bone insufficiency.

7. The method of claim 1, wherein said systemic administration is oral administration.

8. The method of claim 1, wherein said composition comprises said 4-AP or a pharmaceutically acceptable salt thereof.

9. The method of claim 1, wherein said mammal has said osteoporosis.

\* \* \* \* \*